United States Patent [19]

Schirlin

[11] Patent Number: 5,114,927
[45] Date of Patent: May 19, 1992

[54] ANALOG OF PEPTIDASE SUBSTRATES

[75] Inventor: Daniel G. Schirlin, Bischheim, France

[73] Assignee: Merrell Dow Pharmaceuticals Inc., Cincinnati, Ohio

[21] Appl. No.: 759,057

[22] Filed: Sep. 5, 1991

Related U.S. Application Data

[63] Continuation of Ser. No. 422,255, Oct. 16, 1989, abandoned.

[30] Foreign Application Priority Data

Oct. 28, 1988 [EP] European Pat. Off. ............ 88402735

[51] Int. Cl.$^5$ .......................... C07K 5/08; C07K 5/10
[52] U.S. Cl. .................................... 514/18; 530/330; 530/331
[58] Field of Search .................... 514/18, 19; 530/337, 530/330

[56] References Cited

U.S. PATENT DOCUMENTS 4,518,528  5/1985  Rasnick .

FOREIGN PATENT DOCUMENTS 0195212  9/1986  European Pat. Off. .
0204571 12/1986  European Pat. Off. .
86/06379 11/1986  World Int. Prop. O. .
87/04349  7/1987  World Int. Prop. O. .

OTHER PUBLICATIONS

Burger, *Medicinal Chemistry*, 1960, pp. 565–571, 578–581, 600–601.
Denkewalter et al., *Progress In Drug Research*, 1966, vol. 10, pp. 610–612.
Plattner et al., *J. Med. Chem.*, 1988, 31(12):2277–2288.
Bolis et al., *J. Med. Chem.*, 1987, 30(10):1729–1737.
Haber et al., *J. Cardiovasc. Pharmacol.*, 1987, 10(Suppl. 7):554–558.
Schirlin, D. et al., *Tetrahedron Letters*, vol. 29, No. 30, pp. 3687–3690 (1988).
Fearon, K. et al., *J. Med. Chem.*, 30, pp. 1617–1622 (1987).
Thaisrivongs, S. et al., *J. Med. Chem.*, 28, pp. 1555–1558 (1985).
Thaisrivongs, S. et al., *J. Med. Chem.*, 30, pp. 1837–1842 (1987).
Gelb, M. H. et al., *Biochemistry*, 24, No. 8, pp. 1813–1817 (1985).
Imperiali, B. et al., *Biochemistry*, 25, pp. 3760–3767 (1986).
Thaisrivongs, S. et al., *J. Med. Chem.*, 29, pp. 2080–2087 (1986).

*Primary Examiner*—Lester L. Lee
*Attorney, Agent, or Firm*—Stephen L. Nesbitt

[57] ABSTRACT

This invention relates to novel analogs of certain peptidase substrates in which the nitrogen atom of the scissile amide bond has been replaced with a difluoromethylene moiety and in which the carbonyl moiety of its adjacent amide bond has been replaced with a terminal amine function, said novel analogs having the property of inhibiting renin and which are useful in the treatment of hypertension.

2 Claims, No Drawings

ANALOG OF PEPTIDASE SUBSTRATES

CROSS-REFERENCE TO RELATED APPLICATION

This is a continuation of application Ser. No. 07/422,255, filed Oct. 16, 1989 and now abandoned.

This invention relates to novel analogs of certain peptidase substrates in which the nitrogen atom of the scissile amide bond has been replaced with a difluoromethylene moiety and in which the carbonyl moiety of its adjacent amide bond has been replaced with a terminal amine function, said novel analogs having the property of inhibiting renin and which are useful in the treatment of hypertension.

In general, this invention relates to inhibitors of renin having the structural formula

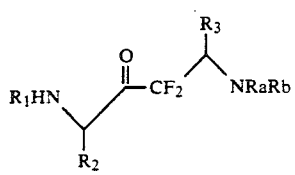

wherein
- $R_1$ is an α-amino acid or peptide, optionally bearing a protecting group on its terminal nitrogen atom,
- $R_2$ is a saturated hydrocarbyl moiety or is the residue of a characteristic α-amino acid responsible for directing the inhibitor to the active site of the enzyme,
- $R_3$ is the residue of a characteristic α-amino acid or a saturated hydrocarbyl moiety,
- Ra and Rb are activity enhancing moieties.

Before further defining and/or illustrating the scope of the peptidase inhibitors embraced by formula I, it may be convenient to state some of the concepts related to peptides, particularly as it may aid in the reading and understanding of this text and formulae involved herein. For example, except for proline, all of the α-amino acids found in proteins have as a common denominator a free carboxyl group and a free unsubstituted amino group on the α-carbon atom (in proline, since proline's α-amino group is substituted it is really an α-imino acid, but for convenience, it will also be spoken of as an α-amino group). Additionally, each α-amino acid has a characteristic "R-group", the R-group being the side chain, or residue, attached to the α-carbon atom of the α-amino acid. For example, the R-group side chain for glycine is hydrogen, for alanine it is methyl, for valine it would be isopropyl. Thus, throughout this specification the $R_2$ or $R_3$ moiety is the residue for each indicated α-amino acid. The specific residues of the α-amino acids are well known in the art.

As a further convenience for defining the scope of the compounds embraced by the generic concept of formula I, as well as the sub-generic concepts relating to each of the individual α-amino acids involved in this invention, various α-amino acids have been classified into a variety of groups which impart similar functional characteristics. These groups (D, E, F, G and K) and the recognized abbreviations for the α-amino acids are set forth in Tables I and II, respectively.

TABLE I

C: Ser, Thr, Gln, Asn, Cys, His, (3-pyrazolyl)Ala, and (4 pyrimidinyl)Ala, and their N-methyl derivatives, D: Pro, Ind, E: Ala, β-Ala, Leu, Ile, Val, n-Val, β-Val, Met, n-Leu and their N-methyl derivatives, F: Phe, Tyre, O-Methyl Tyrosine, (3-pyrazolyl)Ala, (4-pyrimidinyl)Ala, Trp, Nal(1), and their N-methyl derivatives, G: Gly, Sar, K: Acetyl (Ac), Succinyl (Suc), Benzoyl (Bz), t-Butyloxycarbonyl (Boc), Carbobenzoxy (CBZ), Tosyl (Ts), Dansyl (DNS), Isovaleryl (Iva), Methoxysuccinyl (MeOSuc), 1-Adamantanesulphonyl (AdSO$_2$), 1-Adamantaneacetyl (AdAc), 2-Carboxybenzoyl (2-CBZ), Phenylacetyl, t-Butylacetyl (Tba), bis[(1-naphthyl)methyl]acetyl (BNMA) or —A—Rz wherein A is

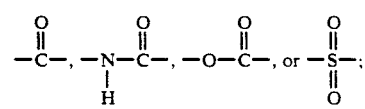

and Rz is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolo, and acylsulfonamido (i.e., acylaminosulfonyl and sulfonylaminocarbonyl) containing from 1 to 15 carbons, provided that when the acylsulfonamido contains an aryl, the aryl may be further substituted by a member selected from fluoro, chloro, bromo, iodo and nitro: and such other terminal amino protecting groups which are functionally equivalent thereto.

TABLE II

| | |
|---|---|
| Alanine | Ala |
| Arginine | Arg |
| Asparagine | Asn |
| Aspartic acid | Asp |
| Asn + Asp | Asx |
| Cysteine | Cys |
| Glutamine | Gln |
| Glutamic acid | Glu |
| Gln + Glu | Glx |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |
| Norvaline | n-Val |
| Norleucine | n-Leu |
| 1-Naphthylalanine | Nal(1) |
| 2-Indolinecarboxylic acid | Ind |
| Sarcosin | Sar |

Throughout this specification, specific compounds may be defined using the shorthand expression $R_1R_2[CF_2R_3NRaRb]$. In this formula it is quite obvious that the bracketed CF$_2$R$_3$NRaRb moiety is the modified α-amino acid of the P′$_1$-position wherein its nitrogen atom has been replaced with a CF$_2$ moiety, its carbonyl moiety has been replaced by the NRaRb moiety, and R$_3$ represents the residue or substituent attached to the α-carbon atom (not shown) of the so-modified P′$_1$-amino acid. Of course, R$_2$ represents the α-amino acid in the P$_1$ position and the R$_1$ moiety represents the α-amino acid or peptide (comprised of up to 4 α-amino acids) in the P$_2$ or the P$_2$ up to P$_5$ positions, respectively, the terminal α-amino acid of which optionally bears an amino protecting group on its nitrogen atom. For example, the compound written as CBZ-His-β-Val-Phe-n-Leu-Leu-[CF$_2$ Gly NHCH$_3$] is a compound wherein the amino group in the α-position of the terminal α-amino acid of the R$_1$ moiety (i.e. histidine) has a carbobenzoxy (CBZ) protecting group, the P$_4$ position α-amino acid is β-Val, the P$_3$-position α-amino acid is Phe, the P$_2$-position α-amino acid is n-Leu, Leu is the P$_1$-position α-amino acid and the [CF$_2$GlyNHCH$_3$] moiety of the P′$_1$-position α-amino acid illustrates the case in which the nitrogen atom has been replaced by difluoromethylene, and the NHCH$_3$ is the monomethylamino moiety wherein Ra is methyl and Rb is hydrogen which has replaced the carbonyl moiety of the P′$_1$-position α-amino acid, which in this instance is glycine. In the manner of the structures of Formula I the same compound would otherwise be written as

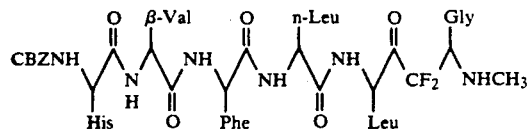

wherein, of course, the designated His, β-val, Phe, n-Leu, Leu, Gly moieties represent the R-group residue attached to the α-carbon atom of that α-amino acid.

Still more specifically, the novel compounds capable of inhibiting renin which are embraced by this invention are compounds of the formula

the hydrates, isosteres or pharmaceutically acceptable salts thereof, wherein

R$_1$ is Phd 2P$_3$P$_4$P$_5$ or P$_2$P$_3$P$_4$P$_5$P$_g$, P$_g$ being a Group K terminal amino protecting group, preferably CBZ, Tba or Iva, P$_2$ is an α-amino acid of Groups C, E or F or is

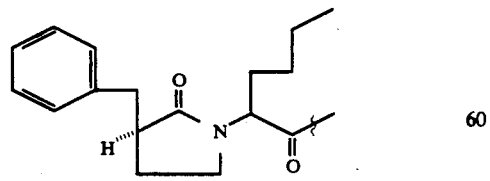

preferably n-Val, n-Leu, His, (3-pyrazolyl)Ala or (4-pyrimidinyl)Ala,

P$_3$ is an α-amino acid of Groups E or F, or is deleted, preferably Nal(1), Phe or O-methyl tyrosine, P$_4$ is deleted or is an α-amino acid of Groups D, E or F, preferably Pro, β-Ala or β-Val, P$_5$ is deleted or is an α-amino acid of Groups C, E or F, preferably His, R$_2$ is a residue of an α-amino acid of Groups E or F, C$_{1-6}$ alkyl, benzyl, cyclohexylmethyl, phenethyl or 2-pyridylmethyl, preferably Leu or cyclohexylmethyl, R$_3$ is a residue of an α-amino acid of Groups E, F or G, C$_{1-6}$ alkyl, benzyl, cyclohexylmethyl, phenethyl or 2-pyridylmethyl, preferably residues of Groups E and G, most preferably Gly, Val, n-Val or n-Leu, Ra is H, a residue of an α-amino acid of Groups E, F or G, C$_{1-6}$ alkyl, benzyl. cyclohexylmethyl or phenethyl, preferably Gly, Leu, n-Val or Ile, Rb is H or a C$_{1-6}$ alkyl, preferably H, said Groups C, D, E, F, G and K being comprised:

C: Ser, Thr, Gln, Asn, Cys. His, (3-pyrazolyl)Ala, (4-pyrimidinyl)Ala, and their N-methyl derivatives, D: Pro and Ind, E: Ala, β-Ala, Leu, Ile, Val, n-Val, β-Val, Met, n-Leu and their N-methyl derivatives, F: Phe, Tyr, O-Methyl Tyrosine. (3-pyrazolyl)Ala, (4 pyrimidinyl)Ala, Trp, Nal(1), and their N-methyl derivatives, G: Gly, Sar, K: Acetyl (Ac), Succinyl (Suc), Benzoyl (Bz), t-Butoxyloxycarbonyl (Boc), Carbobenzoxy (CBZ), Tosyl (Ts), Dansyl (DNS), Isovaleryl (Iva), Methoxysuccinyl (MeOSuc), 1-Adamantanesulphonyl (AdSO$_2$), 1-Adamantaneacetyl (AdAc), 2-Carboxybenzoyl (2-CBZ), Phenylacetyl, t-Butylacetyl (Tba), bis[(1-naphthyl)methyl]acetyl (BNMA),

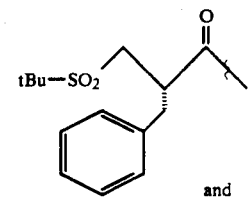

and

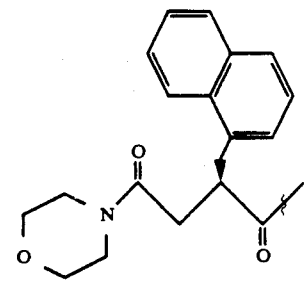

or —A—R$_z$ wherein A is

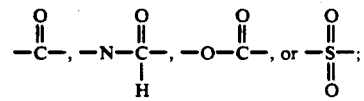

and R$_z$ is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolo, and acylsulfonamido containing from 1 to 15 carbons, provided that when the acylsulfonamido contains an aryl, the aryl may be further substituted by a member selected from fluoro, chloro, bromo, iodo and nitro.

Isosteres of the compounds of Formula I include those wherein (a) one or more of the α-amino residues of the $R_1$ and Q substituents are in their unnatural configuration (when there is a natural configuration) or (b) when the normal peptidic carbamoyl linkage is modified, such as for example, to form —$CH_2NH$— (reduced), —$COCH_2$— (keto), —$CH(OH)CH_2$— (hydroxy), —$CH(NH_2)CH_2$— (amino), —$CH_2CH_2$ —, —CH=CH—(trans) (hydrocarbon). Preferably a compound of the invention should not be in an isosteric form. In those instances wherein Group K represents an —A—Rz moiety, it is preferred that A represent —C(=O)— and that Rz represent acylsulfonamido, particularly those wherein the acylsulfonamido contains an aryl moiety (preferably phenyl) substituted by a halogen, the preferred —A—Rz— moieties being 4-[(4-chlorophenyl)sulfonylaminocarbonyl]phenylcarbonyl, 4-[(4-bromophenyl)sulfonylaminocarbonyl]phenylcarbonyl and 4-[phenylsulfonylaminocarbonyl]-phenylcarbonyl (said moieties being abbreviated as Clϕ-SAC-Bz-Brϕ-SAC-Bz and ϕ-SAC-Bz, respectively).

A compound of the invention may be in free form, e.g., amphoteric form, or in salt, e.g., acid addition, alkali metal, or anionic (e.g., ammonium) salt form. A compound in free form may be converted into a salt form in an art-known manner and vice-versa. Examples of salt forms are the trifluoroacetate, hydrochloride, sodium, potassium and ammonium forms. Unless otherwise stated, the α-amino acid building blocks of these peptidase substrate analogs are preferably in their L-configuration. Of course, it is also understood that in those instances wherein the carbonyl moiety of $P_1$ is in its reduced form, then such compounds are not hydrates.

In those instances wherein the normal R-group residue of an α-amino acid contains an —OH radical (e.g. serine, threonine and tyrosine), it is to be understood that such radical can be derivatized. For example, in each of the foregoing instances the —OH radical can be converted to an ether. When so converted, such as for example to their methyl ethers, then such radicals will be referred to as O-methyl serine, O-methyl threonine and O-methyl tyrosine, respectively. These methyl ether containing side chains may also be depicted as

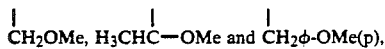
$CH_2OMe$, $H_3CHC$—OMe and $CH_2\phi$-OMe(p), respectively. Similarly, other type derivatives (e.g., N-alkyl derivatives) may also be analogously represented.

As used herein the term "alkyl" includes the straight, branched chain and cyclized manifestations thereof, particularly such moieties as methyl, ethyl, n-butyl, t-butyl, cyclopropyl, n-propyl, pentyl, cyclopentyl, n-hexyl, cyclohexyl and cyclohexylmethyl. The term "aralkyl" includes those aryl moieties attached to a $C_{1-4}$ alkylene, preferably methyl or ethyl. The term "aryl" includes both carbocyclic and heterocyclic moieties.

Preferred aralkyl and aryl moieties are phenyl, benzyl, naphthylmethyl, phenethyl, 2-pyridylmethyl.

The compounds of Formula I inhibit renin and therefore are used as antihypertensive agents useful in treating hypertension. For their end-use application, the potency and other biochemical parameters of the enzyme inhibiting characteristics of the compounds of Formula I are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg/kg per day for an effective therapeutic effect with 0.1 mg to 10 mg/kg per day being preferred. The preferred compounds are:

5-Cyclohexyl-2,2-difluoro-$N^4$-[N-isovaleryl-L-(O-methyl)-Tyrosyl-L-n-Valyl]-3-oxo-1,4-pentanediamine, hydrochloride, 5-Cyclohexyl-2,2-difluoro-$N^1$-isoamyl-$N^4$-[N-isovaleryl-L-(O-methyl)Tyrosyl-L-n-Valyl]-3-oxo-1,4-pentanediamine, hydrochloride, 1-Cyclohexyl-4,4-difluoro-$N^2$-[N-isovaleryl-L-(O-methyl) Tyrosyl-L-n-Valyl]3-oxo-2,5-octanediamine, hydrochloride, 1-Cyclohexyl-4,4-difluoro-$N^2$-[N-tert-butylacetyl L-(O-meth yl)Tyrosyl-L-n-Valyl]7 methyl-3-oxo-2,5-octanediamine, hydrochloride, 1-Cyclohexyl-4,4-difluoro-$N^2$-[N-tert-butylacetyl-L-(O-methyl)Tyrosyl L-n-Valyl]6 methyl 3-oxo-2,5-heptanediamine, hydrochloride, 5-Cyclohexyl-2,2-difluoro-$N^4$-[N-isovaleryl-L-(1-naphthyl)-alanine L-n-Valyl]3-oxo-1,4-pentanediamine, hydrochloride, 5-Cyclohexyl-2,2-difluoro-$N^4$-[N-(1-tert-butylsulfonyl-methyl-3-phenyl-propanoyl)-L-n-Valyl]-3-oxo-1,4-pentanediamine, hydrochloride, 5-Cyclohexyl-2,2-difluoro-$N^4$-[N-isovaleryl-L-(O-methyl)-Tyrosyl-L-(N-methyl)-n-Valyl]-3-oxo-1,4-pentanediamine, hydrochloride, 5-Cyclohexyl-2,2-difluoro-$N^4$-[N-isovaleryl-L-Phenylalanyl-L-(N-methyl)-n-Valyl]-3-oxo-1,4-pentanediamine, hydrochloride, 5-Cyclohexyl-2,2-difluoro-$N^1$-isoamyl-$N^4$-[N-isovaleryl L-(O-methyl)-Tyrosyl-L-(N-methyl) n-Valyl]-3-oxo-1,4-pentanediamine, hydrochloride, 1-Cyclohexyl-4,4-difluoro-$N^2$-[N tert-butylacetyl-L-(O-methyl) Tyrosyl-L-(N-methyl)-n-Valyl]6-methyl-3-oxo-2,5-heptanediamine, hydrochloride.

Having defined the scope of compounds within the generic aspect of this invention and within the individual subgeneric groups, as well as the preferred specific compounds, the manner in which such may be prepared is described and illustrated by the following generic and specific teachings.

In general, the compounds of formula I may be prepared by using standard chemical reactions analogously known in the art. The key intermediates required for the application of standard peptide coupling techniques may be represented by the formula Va or Vb

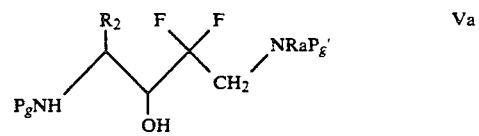

-continued

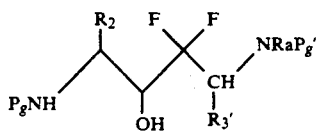

wherein

R$_3$' is as defined for R$_3$, except that it is other than H and it may also be a protected form of the residue of the specific α-amino acid involved, R$_2$ is as previously defined, and P$_g$ and P$_g$' are each protecting groups, preferably different from each other so as to facilitate selective removal depending upon the site, nature and sequence of the reactions required to prepare the final compounds from these intermediates: the selection being according to principles well known and understood by those of ordinary skill in the art.

In those instances of Formula I wherein R$_3$ represents hydrogen the preparation of the required intermediates (Va) is illustrated by Reaction Scheme A. In those instances of Formula I wherein R$_3$ is other than hydrogen then the required intermediates (Vb) are prepared by the methods depicted in Reaction Scheme B.

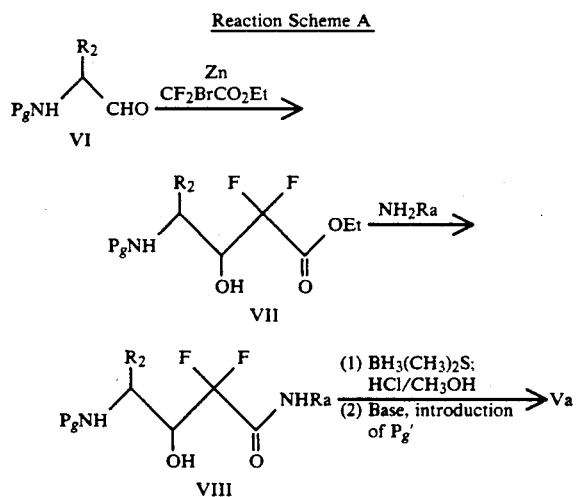

wherein P$_g$ is an amine protecting group, and R$_2$ and Ra are as previously defined.

In effecting the steps of Reaction Scheme A it is preferred to start with the aldehyde of formula VI wherein the protecting group is a carbamate preferably wherein P$_g$ is benzyloxycarbonyl (CBZ). This so-protected aldehyde is subjected to a condensation reaction with an ester of bromodifluoroacetic acid, preferably the ethyl ester in the presence of zinc. Preferably the reaction is conducted in an anhydrous aprotic solvent, e.g., tetrahydrofuran, ether, dimethoxyethane and the like under a nitrogen or argon atmosphere. The reaction mixture is gently heated under reflux conditions, preferably to about 60° C. for about 1-12 hours. The ester (VII) is converted to its amide (VIII) by treatment with the appropriate amine or liquid ammonia under anhydrous conditions, preferably using such solvents as anhydrous diethyl ether. The amidation is initiated at −78° C. and following saturation with ammonia the reaction mixture is slowly allowed to rise to room temperature, or after addition of the RaNH$_2$ amine the mixture is refluxed in tetrahydrofuran. The so-formed amide is chemically reduced by reacting the amide with a diborane, preferably as a diborance/dimethylsulfide complex, under a nitrogen atmosphere in an anhydrous aprotic solvent (e.g., THF) under reflux conditions. The reduction yields the desired amine, in the form of an acid (e.g., HCl) salt which (after the usual work-up) by pH adjustment yields the base which may be suitably protected with an N-protecting group, e.g., P$_g$' is t-butoxy carbonyl using the standard reaction conditions (e.g., (BOC)$_2$O, tetrahydrofuran at room temperature) for protecting the amine.

In those instances where R$_3$' is other than hydrogen then the procedure of Reaction Scheme A is modified to prepare the desired intermediates according to Reaction Scheme B

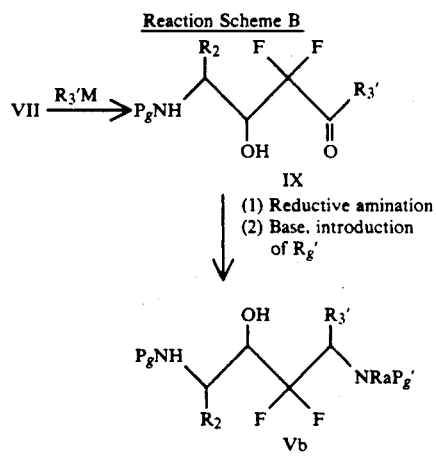

wherein R$_3$'M is an organometallic reagent, preferably lithium or magnesium coupled to the R$_3$' moiety desired.

The conversion of the ester (VII) to the corresponding R$_3$' bearing ketone with the organometallic reactant is effected by contacting the reactants together under anhydrous conditions at temperatures of about 0° to −80° C. in an aprotic solvent (e.g., tetrahydrofuran). Upon reaction the temperature is slowly allowed to rise to room temperature and the complex is hydrolysed to yield the desired intermediate ketones (IX) which compounds are subjected to reductive amination procedures well known in the art, such as, for example, the procedure described by Borch (see R. F. Borch, et al., *J. Am. Chem. Soc.*, 93, 2897 (1971). This reductive amination can take place in one or two steps (with isolation of the intermediate imine or enamine). For example, reacting the ketones (IX) with ammonium acetate under slightly acidic conditions in methanol produces the enamine which, when reacted with sodium cyanoborohydride, produces the desired product. Alternatively, the ketones may be treated directly with sodium cyanoborohydride in the presence of ammonium acetate to produce the desired amines (as its HCl salts) which, in either case, may be neutralized and then the NH$_2$ moiety may be protected with an appropriate protecting group.

In those instances wherein the desired compounds contain Ra and Rb moieties both of which are other than H, then such compounds may be prepared by procedures well known in the art. In this reaction sequence the protecting group of the (—NRaP$_g$') moiety is selectively cleared by standard amine deprotecting procedures to produce intermediate compounds bearing the moiety (—NHRa) which, when reacted with the appropriate acyl chloride, produces the intermediate amide (—NRaCOR'b) moiety which, when reduced with a borane, preferably with borone demethylsulfide, yields the desired (—NRaR'b) moiety (R'b being Rb other than H). This reaction sequence is illustrated by the following partial-structure reaction scheme showing the preparation of a compound wherein Ra is ethyl (Et) and Rb is methyl:

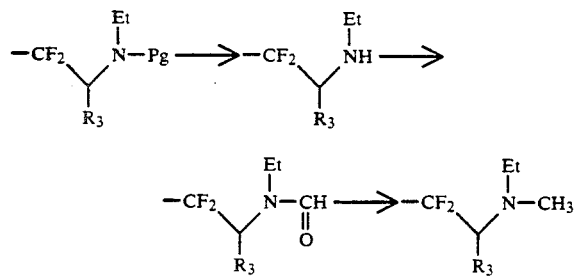

Having obtained the key intermediates of formula V (a and b) standard α-amino acid or peptide coupling procedures may be conducted to prepare the individual compounds of formula I. In general, this series of reactions may be depicted by Reaction Reaction Scheme C.

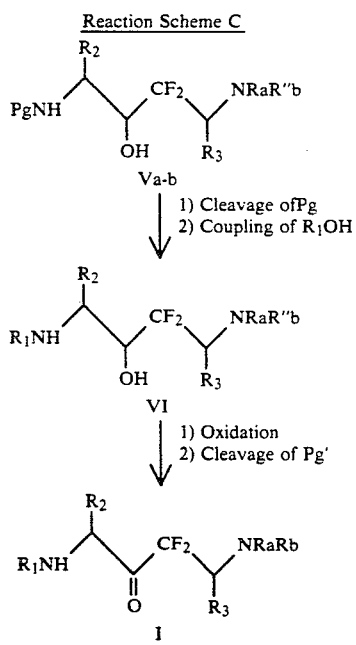

wherein $R_1$, $R_2$, $R_3$, Ra and $P_g$ are as previously defined and $R_1OH$ is the equivalent to $RCO_2H$, and $R_b''$ is Rb or $P_{g'}$ with $R_b$ and $P_g$ being as previously defined.

The cleavage of the protecting groups may be effected by any of the standard techniques known in the art, such as those illustrated in the specific hereinafter disclosed examples. Similarly, the coupling procedures after cleavage of the Pg protecting group may be effected according to standard procedures well known in the art.

The oxidation may be effected via the well known Swern oxidation procedure, or with a modified Jones reaction using pyridinium dichromate, or a chromic anhydride-pyridinium complex, or with 1,1,1-triacetoxy-2,1-benzoxiodol. Of course, if there are any protecting groups on the residues of the α-amino acid building blocks, such protecting groups may be removed after oxidation.

In general the Swern oxidation is effected by reacting about 2 to 10 equivalents of dimethylsulfoxide (DMSO) with about 1 to 6 equivalents of trifluoromethylacetic anhydride [$(CF_2CO)_2O$] or oxalyl chloride [$(COCl)_2$], said reactants being dissolved in an inert solvent, e.g., methylene chloride ($CH_2Cl_2$), said reactor being under an inert atmosphere (e.g., nitrogen or equivalently functioning gas) under anhydrous conditions at temperatures of about $-80°$ C. to $-50°$ C. to form an in situ sulfonium adduct to which is added about 1 equivalent of the appropriate alcohols (VI).

Preferably, the alcohols are dissolved in an inert solvent, e.g., $CH_2Cl_2$ or minimum amounts of DMSO, and the reaction mixture is allowed to warm to about $-50°$ C. (for about 10-20 minutes) and then the reaction is completed by adding about 3 to 10 equivalents of a tertiary amine, e.g., triethyl amine, N-methyl morpholine, etc.

In general, the modified Jones oxidation procedure may conveniently be effected by reacting the alcohols (VI) with pyridinium dichromate in dichloromethane by contacting the reactants together in a water-trapping molecular sieve powder, e.g., a grounded 3-Angstrom molecular sieve), wherein said contact is in the presence of glacial acetic acid at about 0° C. to 50° C., preferably at room temperature followed by isolation and then optionally removing amine protecting groups.

Alternatively, 1 to 5 equivalents of a chromic anhydride pyridine complex (i.e., a Sarett reagent prepared in situ (see Fieser and Fieser "Reagents for Organic Synthesis" Vol. 1, pp. 145 and Sarett, et al., J.A.C.S. 25, 422, (1953)) said complex being prepared in situ in an inert solvent (e.g., $CH_2Cl_2$) in an inert atmosphere under anhydrous conditions at 0° C. to 50° C. to which complex is added 1 equivalent of the alcohols (VI) allowing the reactants to interact for about 1 to 15 hours, followed by isolation and optionally removing amine protecting groups.

Another alternative process for converting the alcohols (VI) to the desired ketones is an oxidation reaction which employs periodane (i.e., 1,1,1-triacetoxy-2,1-benzoxiodol, (see Dess Martin, J. Org. Chem., 48. 4155, (1983)). This oxidation is effected by contacting about 1 equivalent of the alcohols (VI) with 1 to 5 equivalents of periodane (preferably 1.5 equivalents), said reagent being in suspension in an inert solvent (e.g., methylene chloride) under an inert atmosphere (preferably nitrogen) under anhydrous conditions at 0° C. to 50° C. (preferably room temperature) and allowing the reactants to interact for about 1 to 48 hours. Optional deprotection of the amine protecting groups may be effected as desired after the ketones have been isolated.

The following specific examples are given to illustrate the preparation of the compounds of this invention.

EXAMPLE 1

4

Benzyloxycarbonylamino-2,2-difluoro-3-hydroxy-6-methylheptanoic acid, ethyl ester A mixture of 2.080 g (8.3 mmol) of L-N benzyloxycarbonyl Leucinal and 2,230 g (11 mmol) of ethyl bromodifluoroacetate in dry tetrahydrofuran (15 mL) was added dropwise to a refluxing suspension of 0.710 g of activated zinc wool in dry tetrahydrofuran (10 mL), under nitrogen. The addition rate was adjusted to maintain gentle reflux of the mixture. After the addition was complete, the solution was stirred for 3 hours at room temperature. The mixture was quenched by addition of 20 mL ethyl acetate, brine and 1M KHSO$_4$ (20 mL). The aqueous layer was dried over anhydrous MgSO$_4$, evaporated and purified by flash chromatography (silica gel, ethylacetate/cyclohexane: 1:9). 1.130 g of the expected ester were isolated (yield: 36%) (colorless oil).

Rf: 0.57 (ethyl acetate/cyclohexane, 1:1).

EXAMPLE 2

4-Benzyloxycarbonylamino-2,2-difluoro-3-hydroxy-6-methylheptanamide

A stream of dry ammonia was bubbled at −78° C., through a solution of 0.820 g (2.2 mmol) of 4-benzyloxycarbonylamino-2,2-difluoro-3-hydroxy-6-methylheptanoic acid, ethyl ester in anhydrous diethyl ether (10 mL). After saturation, the temperature was allowed to rise to room temperature with stirring. The excess ammonia was removed, and the solvent evaporated in vacuo. The residue was taken off in pentane to yield the expected amide in quantitative yield as a solid.

MS(CI/NH$_3$): 345 (MH+).

EXAMPLE 3

N$^4$-Benzyloxycarbonyl-N$^1$-tert-butoxycarbonyl-2,2-difluoro-3hydroxy-6-methyl-1,4-heptanediamine A solution of 1M BH$_3$/(CH$_3$)$_2$S (1 mL) in dichloromethane was added, under nitrogen, to a mixture of 0.185 g (0.53 mmol) of 4-benzyloxycarbonylamino-2,2-difluoro-3-hydroxy-6-methylheptanamide in anhydrous tetrahydrofuran (10 mL). The mixture was heated at reflux for 3 hours. After cooling to room temperature, methanol (3 mL) and 1N HCl in diethyl ether (6 mL) were added. The solvent was removed in vacuo. The residue was taken off in water and the aqueous layer washed with diethyl ether. The pH of the aqueous phase was adjusted to 10. Diethyl ether extraction afforded the intermediate amine which was directly converted to its N-BOC protected form [(BOC)$_2$O 1.5 eq; tetrahydrofuran; room temperature]. The expected tert. butylcarbamate was purified by chromatography (silica gel, ethyl acetate/cyclohexane, 1:1), 0.180 g (79% yield).

Rf: 0.63 (ethyl acetate/cyclohexane, (1:1).

EXAMPLE 4

4-Benzyloxycarbonylamino-2,2-difluoro-3-hydroxy-5-phenylpentanoic acid, ethyl ester The title compound was prepared from L-N-benzyloxy carbonylphenylalaninal and ethyl bromodifluoroacetate by the procedure described in Example 1 (75% yield).

Rf: 0.5 (ethyl acetate/cyclohexane, 1:1).

Analysis calculated for C$_{21}$H$_{23}$NO$_5$F$_2$ C%: 61.91: H%: 5.69; N%: 3.44 found C%: 62.19; H%: 5.75; N%: 3.55

EXAMPLE 5

4-Benzyloxycarbonylamino-2,2-difluoro-3-hydroxy-5-phenylpentanamide

The title compound was prepared from the ester of Example 4 by the procedure described in Example 2 (98% yield).

EXAMPLE 6

N$^4$-Benzyloxycarbonyl-N$^1$-tert-butoxycarbonyl-2,2-difluoro-3 hydroxy-5-phenyl-1,4-pentanediamine The title compound was prepared from the amide of Example 5 by the procedure described in Example 3 (64% yield).

EXAMPLE 7

N$^1$-tert Butoxycarbonyl-2,2-difluoro-3-hydroxy-5-phenyl-1,4-pentanediamine

A solution of N$^4$-benzyloxycarbonyl-N$^1$-tert-butoxycarbonyl-2,2-difluoro-3-hydroxy-5-phenyl-1,4-pentanediamine (0.464 g, 1 mmol) in ethanol (20 mL) was stirred at room temperature in the presence of 10% Palladium on charcoal (0.020 g) under a hydrogen atmosphere for 5 hours. The hydrogen atmosphere was then replaced by a nitrogen atmosphere and the catalyst was filtered. The solvent was removed in vacuo leaving 0.030 g of the expected product (98% yield).

EXAMPLE 8

4-Benzyloxycarbonylamino-2,2-difluoro-3-hydroxy-5-methylhexanoic acid, ethyl ester The title compound was prepared from L-N-benzyloxycarbonylvalinal and ethyl bromodifluoroacetate by the procedure described in Example 1. (40% yield)

EXAMPLE 9

4-Benzyloxycarbonylamino-2,2-difluoro-3-hydroxy-5-methylhexanamide

The title compound was prepared in quantitative yield from the ester of Example 8 by the procedure described in Example 2.

EXAMPLE 10

N$^4$-Benzyloxycarbonyl-N$^1$-tert-butoxycarbonyl-2,2-difluoro-3-hydroxy-5-methyl-1,4-hexanediamine The title compound was prepared from the amide of Example 9 by the procedure described in Example 3 (yield: 40%).

Rf: 0.50 (ethyl acetate/cyclohexane, 1:1).

EXAMPLE 11

N$^1$-tert-Butoxycarbonyl-2,2-difluoro-3-hydroxy-5-methyl-1,4-hexanediamine

The title compound was prepared in quantitative yield from the dicarbamate of Example 10 by the procedure described in Example 7.

EXAMPLE 12

Ethyl 4-benzyloxycarbonylamino-2,2-difluoro-3-hydroxy butanoate

The title compound was prepared in 33% yield from N-benzyloxycarbonylglycinal, ethyl bromodifluoroacetate and zinc by the procedure described in Example 1.

Rf: 0.45 (silica gel; ethyl acetate/cyclohexane 1:1).

EXAMPLE 13

The title compound was prepared in 95% yield from the ester of Example 12 by the procedure described in Example 2.

Rf: 0.49 (silica gel; ethyl acetate/cyclohexane 1:1).

EXAMPLE 14

$N^4$-Benzyloxycarbonyl-$N^1$-(tert-butoxycarbonyl)-2,2-difluoro-3-hydroxy-1,4-butanediamine The title compound was prepared in 48% yield from the amide of Example 13 by the procedure described in Example 3.

Rf: 0.42 (silica gel; ethyl acetate/cyclohexane 1:1). MS(DCI/CI+/NH$_3$): 392(MNH$^+_4$, 59); 375(MH$^+$, 20); 258(15); 241(100).

EXAMPLE 15

Ethyl 4-benzyloxycarbonylamino-2,2-difluoro-3-hydroxy pentanoate

The title compound was prepared in 50% yield from N-benzyloxycarbonylalaninal, ethyl bromodifluoroacetate and zinc by the procedure described in Example 1.

Rf: 0.49 (silica gel; ethyl acetate/cyclohexane 1:1).

EXAMPLE 16

4-Benzyloxycarbonylamino-2,2-difluoro-3-hydroxy pentanamide

The title compound was prepared in 90% yield from the ester of Example 15 by the procedure described in Example 2.

Rf: 0.50 (silica gel; ethyl acetate/cyclohexane 1:1). MS(DCI/CI+/NH$_3$) 392(MNH$^+_4$, 100); 303(MH$^+$, 13); 212(19): 169(100).

EXAMPLE 17

$N^4$-Benzyloxycarbonyl-$N^1$-(tert-butoxycarbonyl)-2,2-difluoro-3-hydroxy-1,4-pentanediamine The title compound was prepared in 53% yield from the amide of Example 16 by the procedure described in Example 3.

Rf: 0.47 (silica gel; ethyl acetate/cyclohexane 1:1). MS(DCI/CI+/NH$_3$): 406(MNH$^+_4$, 94); 389(MH$^+$, 23): 298(20): 255(100).

EXAMPLE 18

N-Benzyloxycarbonyl-3-cyclohexylalanine

To a solution of 3-cyclohexylalanine, hydrochloride (4.75, 22.8 mmol) in 2N sodium hydroxide (11.4 mL) were added at 0° C., simultaneously, a solution of benzylchloroformate (3.2 mL, 36 mmol) in tetrahydrofuran (10 mL) and 2N sodium hydroxide (11.4 mL). (The pH of the mixture was maintained around 9-10 by addition of 2N sodium hydroxide.) The mixture was stirred for 1.5 hours. The solution was washed with diethyl ether (3×20 mL). The aqueous phase was acidified to pH 2 with 3N aqueous hydrochloric acid and extracted with ethyl acetate (3×50 mL). The combined organic layers were dried over anhydrous magnesium sulphate. Filtration and removal of the solvent in vacuo left 4.80 g of the expected product (yellow oil, 69% yield).

Rf: 0.75 (silica gel: AcOH/BuOH/H$_2$O 2:6:2).

EXAMPLE 19

2-Benzyloxycarbonylamino-3-cyclohexyl-N,O-dimethyl propanehydroxamate

To a solution of N-benzyloxycarbonyl-3-cyclohexylalanine (4.60 g, 15 mmol) in anhydrous methylene chloride (60 mL) were added, at 0° C., dicyclohexylcarbodiimide (3.09 g, 15 mmol) and 1-hydroxybenzotriazolehydrate (2.29 g, 15 mmol). After stirring for 0.25 hours at 0° C., N,O,-dimethylhydroxylamine hydrochloride (1.46 g, 15 mmol) and N-methylmorpholine (1.51 g, 15 mmol) were added to the mixture. The mixture was stirred for 20 hours while the temperature was allowed to rise to room temperature. The precipitate was filtered off. The solvent was removed in vacuo and the mixture was purified by chromatography (silica gel: ethyl acetate/cyclohexane 2/8) yielding 3.60 g of the expected hydroxamate (69% yield).

Rf:0.38 (silicagel; ethylacetate/cyclohexane 1:1, UV, I$_2$).

EXAMPLE 20

N-Benzyloxycarbonyl-3-cyclohexylalaninal

A mixture of 2-benzyloxycarbonylamino-3-cyclohexyl-N,O-dimethyl propanehydroxamate (3.58 g, 10.3 mmol), and lithium aluminum hydride (0.44 g, 11.6 mmol) in anhydrous diethyl ether (100 mL) was stirred at 0° C. for 1 hour. 1M potassium hydrogenosulphate (25 mL) was added. The mixture was stirred for 0.5 hour and extracted with diethyl ether (2×25 mL). The combined organic layers were washed with 2N HCl (3×20 mL), water (1×20 mL), a saturated solution of sodium bicarbonate (1×20 mL), brine (20 mL) and dried over anhydrous magnesium sulphate. Filtration and removal of the solvent in vacuo left 2.52 g of the expected aldehyde (85%, yellowish oil) used in the next step without further purification.

EXAMPLE 21

4-Benzyloxycarbonylamino-5-cyclohexyl-2,2-difluoro-3-hydroxypentanoic acid, ethyl ester The title compound was prepared in 37% yield from N-benzyloxycarbonyl-3-cyclohexylalaninal, ethyl bromodifluoroacetate and zinc by the procedure described in Example 1.

Rf: 0.57 (silica gel; ethyl acetate/cyclohexane 1:1).

EXAMPLE 22

4-Benzyloxycarbonylamino-5-cyclohexyl-2,2-difluoro-3-hydroxypentanamide

The title compound was prepared in 97% yield from the ester of Example 21 by the procedure described in Example 2.

Rf: 0.53 (silica gel; ethyl acetate). MS(DCI/CI+/NH$_3$): 402(MNH$^+_4$, 86); 385(MH$^+$, 13); 294(23); 169(40); 126(100).

EXAMPLE 23

$N_4$-Benzyloxycarbonyl-$N^1$-(tert-butoxycarbonyl)-5-cyclohexyl-2,2-difluoro-3-hydroxy-1,4-pentanediamine The title compound was prepared in 51% yield from the amide of Example 22 by the procedure described in Example 3.

Rf: 0.59 (silica gel; ethyl acetate/cyclohexane 1:1).

EXAMPLE 24

$N^1$-(tert-butoxycarbonyl)-5-cyclohexyl-2,2-difluoro-3-hydroxy-1,4-pentanediamine The title compound was prepared in 86% yield from the dicarbamate of Example 23 by the procedure described in Example 7.

EXAMPLE 25

$N^1$-(tert-butoxycarbonyl)-5-cyclohexyl-2,2-difluoro-3-hydroxy-$N^4$-[N-isovaleryl-L-(O-methyl)tyrosyl-L-n-valyl]-1,4-pentanediamine To a stirred solution of 0.325 g (0.86 mmol) of N-isovaleryl-L-(O-methyl)tyrosyl-L-n-valine in dry acetonitrile (8 mL), under nitrogen, was added 0.090 g of N-methylmorpholine. The resulting solution was cooled to −20° C. Isobutyl chloroformate (0.117 g, 0.86 mmol) was added dropwise to the cooled reaction mixture. After 10 minutes, a solution of 0.300 g (0.89 mmol) of $N^1$-(tert-butoxycabonyl)-5-cyclohexyl-2,2-difluoro-3-hydroxy-1,4-pentanediamine in dry acetonitrile (3 mL) was added to the cooled mixture. After stirring for 4 hours at −20° C., the temperature of the mixture was allowed to rise to room temperature. Stirring was continued for 15 hours at room temperature. The solvent was then removed in vacuo and the resulting residue was chromatographed (silica gel; ethyl acetate/cyclohexane 1:1) to give the title compound in 61% yield.

Rf: 0.16 (silica gel: ethyl acetate/cyclohexane 1:1). Analysis calculated for $C_{36}H_{58}N_4O_7F_2$ C%: 62.05; H%: 8.39; N%: 8.04 found C%: 62.06: H%: 8.30; N%: 8.00

EXAMPLE 26

$N^1$-(tert-butoxycarbonyl)-5-cyclohexyl-2,2-difluoro-$N^4$-[N-isovaleryl-L-(O-methyl)tyrosyl-L-n-valyl]3-oxo-1,4-pentanediamine A solution of 0.330 g (0.47 mmol) of alcohol of Example 25 in methylene chloride (5 mL) was added to a mixture of pyridinium dichromate (0.314 g), 3A molecular sieves (0.573 g) and glacial acetic acid (0.010 mL) in methylene chloride (10 mL). Stirring was continued for 15 hours at room temperature. The crude mixture was purified by chromatography (silica gel: ethyl acetate/cyclohexane 1:1) to give the title compound in 76% yield as a white solid.

Rf: 0.67 (silica gel; ethyl acetate).

Analysis calculated for $C_{36}H_{56}N_4O_7F_2$ C%: 62,23 H%: 8.12: N%: 8.06 found C%: 62.31; H%: 8.06; N%: 8.16

EXAMPLE 27

5-Cyclohexyl-2,2-difluoro-$N^4$-[N-isovaleryl-L-(O-methyl)-tyrosyl-L-n-valyl]-3-oxo-1,4-pentanediamine, hydrochloride A mixture of 0.207 g (0.3 mmol) of ketone of Example 26 in a saturated solution of hydrogen chloride in diethyl ether (10 mL) and tetrahydrofuran (1 mL) was stirred at room temperature for 15 hours. A white precipitate formed during that time. The solvent was removed in vacuo. The residue was taken off in diethyl ether and evaporated to dryness (three times). The residue was recrystallized from ethanol/diethyl ether, to yield 0.128 g of the title compound (68% yield).

Rf 0.65 (silica gel; AcOH/BuOH/$H_2O$, 2:6:2).

Analysis calculated for $C_{31}H_{48}N_4O_5F_2$ HCl. (1.25 $H_2O$) C%: 56.96; H%: 7.94; N%: 8.57 found C%: 56.89: H%: 7.99; N%: 8.51

EXAMPLE 28

4-Benzyloxycarbonylamino-5-cyclohexyl-2,2-difluoro-3-hydroxy-N-isoamylpentanamide A mixture of 4 benzyloxycarbonylamino-5-cyclohexyl-2,2-difluoro-3-hydroxy pentanoic acid, ethyl ester (0.207 g: 0.5 mmol) and isoamylamine (0.087 g: 1 mmol) in tetrahydrofuran (5 mL) was heated at reflux for 15 hours under nitrogen. Diethyl ether was added. The organic solution was washed with 0.1N HCl and dried over anhydrous magnesium sulphate. Filtration and removal of the solvent in vacuo left a residue which was purified by chromatography (silica gel; ethyl acetate/cyclohexane 1:1). 0.170 g of the expected amide were isolated (75% yield).

EXAMPLE 29

$N^4$-Benzyloxycarbonyl-$N^1$-(tert-butoxycarbonyl)-5-cyclohexyl-2,2-difluoro-3-hydroxy-N-lisoamyl-1,4-pentanediamine The title compound was prepared from the amide of Example 28 by the procedure described in Example 3.

EXAMPLE 30

$N^1$-(tert-Butoxycarbonyl)-5-cyclohexyl-2,2-difluoro-3-hydroxy-$N^1$-isoamyl-1,4-pentanediamine The title compound was prepared in quantitative yield from the dicarbamate of Example 29 by the procedure described in Example 7.

EXAMPLE 31

$N^1$-(tert-Butoxycarbonyl)-5-cyclohexyl-2,2-difluoro-3-hydroxy-$N^1$-isoamyl-$N^1$-[N-isovaleryl-L-(O-methyl)-tyrosyl-L-n valyl]-1,4-pentanediamine The title compound was prepared in 60% yield from N-isovaleryl-L-(O-methyl)tyrosyl-L-n valine and the amine of Example 30 by the procedure described in Example 25.

EXAMPLE 32

$N^1$-(tert-Butoxycarbonyl)-5-cyclohexyl-2,2-difluoro-$N^1$-isoamyl-$N^4$-[N-isovaleryl-L-(O-methyl)tyrosyl-L-n-valyl]3-oxo-1,4-pentanediamine The title compound was prepared from the alcohol of Example 31 by the procedure described in Example 26.

EXAMPLE 33

5-Cyclohexyl-2,2-difluoro-$N^1$-isoamyl-$N^4$-[N-isovaleryl-L-(O-methyl)tyrosyl-L-n-valyl]-3-oxo-1,4-pentanediamine, hydrochloride The title compound was prepared from the carbamate of Example 32 by the procedure described in Example 27.

EXAMPLE 34

4-Benzyloxycarbonylamino-5-cyclohexyl-2,2-difluoro-3-hydroxy pentanoic acid

A solution of 0.023 g (0.55 mmol) of LiOH, H$_2$O in water (1 mL) was added at 0° C. to a mixture of 4-benzyloxycarbonyl amino-5-cyclohexyl-2,2-difluoro-3-hydroxy-pentanoic acid, ethyl ester (0.206 g, 0.5 mmol) in dimethoxyethane (DME) (3 mL). The temperature was allowed to raise slowly to room temperature, and the mixture was stirred at room temperature for 15 hours. The mixture was then diluted with water (5 mL), washed with diethyl ether (10 mL). The aqueous layer was acidified to about pH 2 with 0.1N HCl, extracted with diethyl ether (2×10 mL). The combined organic layers were washed with brine and dried over anhydrous MgSO$_4$. Filtration and removal of the solvent in vacuo yielded the expected acid, recrystallized from diethyl ether/pentane.

EXAMPLE 35

7-Benzyloxycarbonylamino-8-cyclohexyl-5,5-difluoro-6-hydroxy-4-octanone

To a rapidly stirred solution of n-propylmagnesium bromide (9 mmol) in anhydrous diethyl ether (20 mL) was added dropwise a solution of 0.641 g (2,25 mmol) of 4-benzyloxycarbonylamino-5-cyclohexyl-2,2-difluoro-3-hydroxy pentanoic acid in anhydrous diethyl ether (10 mL). The mixture was refluxed under nitrogen for two hours after the addition of the acid was completed. The crude mixture was then poured onto a mixture of ice and 0.2N HCl (50 mL). The layers were separated and the aqueous phase was extracted with diethyl ether (3×20 mL). The combined organic layers were washed with a saturated sodium bicarbonate solution and brine. The organic layer was dried over anhydrous magnesium sulphate. Filtration and removal of the solvent in vacuo left an oil. The residue was purified by chromatography (silica gel, ethyl acetate/cyclohexane 1:1) to yield the expected ketone.

EXAMPLE 36

N$^5$-(tert-Butoxycarbonyl)-N$^2$-benzyloxycarbonyl-1-cyclohexyl-4,4-difluoro-3-hydroxy-2,5-octanediamine A mixture of 7-benzyloxycarbonylamino-8-cyclohexyl-5,5-difluoro-6-hydroxy-4-octanone (0.235 g. 0.46 mmol), ammonium acetate (0.354 g, 4.6 mmol) and sodium cyanoborohydride (0.020 g, 0.32 mmol) in methanol (7 mL) was stirred at room temperature under nitrogen for 20 hours. The mixture was acidified by addition of 1N HCl (4 mL) and the solvent was removed in vacuo. The residue was taken off in water. The aqueous phase was washed with diethyl ether. The pH of the aqueous phase was adjusted to 10. Diethyl ether extraction afforded the free amine which was directly converted to its N-BOC protected form. [(BOC)$_2$O, 1.5 eq; tetrahydrofuran, room temperature]. The expected dicarbamate was purified by chromatography (silica gel: ethyl acetate/cyclohexane 1:1).

EXAMPLE 37

N$^5$-(tert-Butoxycarbonyl)-1-cyclohexyl-4,4-difluoro-3-hydroxy-2,5-octanediamine The title compound was prepared in quantitative yield from the dicarbamate of Example 36, by the procedure described in Example 7.

EXAMPLE 38

N$^5$-(tert-Butoxycarbonyl)-1-cyclohexyl-4,4-difluoro-3-hydroxy-N$^2$-[N-isovaleryl-L-(O-methyl)tyrosyl-L-n-valyl]2,5-octanediamine The title compound was prepared from N-isovaleryl-L-(O-methyl)tyrosyl-L-n-valine and the amine of Example 37 by the procedure described in Example 25.

EXAMPLE 39

N$^5$ (tert-Butoxycarbonyl)-1-cyclohexyl-4,4-difluoro-N$^2$-[N-isovaleryl-L-(O-methyl)tyrosyl-L-n-valyl]-3-oxo-2,5-octanediamine The title compound was prepared from the alcohol of Example 38 by the procedure described in Example 26.

EXAMPLE 40

1-Cyclohexyl-4,4-difluoro-N$^2$-[N-isovaleryl-L-(O-methyl)-tyrosyl-L-n-valyl]3-oxo-2,5-octanediamine, hydrochloride The title compound was prepared from the carbamate of Example 39 by the procedure described in Example 27.

By following the techniques referenced above, as well as by utilization of other known techniques, as well as by comparison with compounds known to be useful for treatment of the above mentioned disease states, it is believed that adequate material is available to enable one of ordinary skill in the art to practice the invention. Of course, in the end-use application of the compounds of this invention, the compounds are preferably formulated into suitable pharmaceutical preparations such as tablets, capsules or elixirs, for oral administration or in sterile solutions or suspensions for parenteral administration. The compounds of this invention can be administered to patients (animals and human) in need of such treatment in divided dosages given several times per day. As stated above, the dose will vary depending on severity of disease, weight of patient and other factors which a person skilled in the art will recognize.

Typically the compounds described above are formulated into pharmaceutical compositions as discussed below.

The necessary amount of a compound or mixture of compounds of formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose: a disintegrating agent such as corn starch, pregelatinized starch, alginic acid and the like: a lubricant such as magnesium stearate: a sweetening agent such as sucrose, lactose or saccharin: a flavoring agent such as peppermint, oil of wintergreen or cherry. When the dosage unit form is a capsule, it may contain in addition to materials of the above type, a liquid carrier such as fatty oil. Various other materials may he present as coatings or to otherwise modify the physical form of the dosage unit. For instance, tablets may be coated with shellac, sugar or both. A syrup or elixer may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil. etc., or a synthetic fatty vehicle like ethyl oleate or the like. Buffers, preservatives. antioxidants and the like can be incorporated as required.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound of the formula

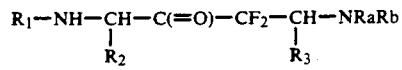

or a pharmaceutically acceptable salt thereof, wherein
$R_1$ is Iva-(O-methyl)Tyr-nVal-;
$R_2$ is cyclohexylmethyl;
$R_3$ is H;
$R_a$ is H; and
$R_b$ is H.

2. A method of treating renin-dependent hypertension which comprises administering to a patient having renin-dependent hypertension a therapeutically effective amount of a compound of the formula

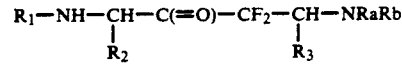

or a pharmaceutically acceptable salt thereof, wherein
$R_1$ is Iva-(O-methyl)Tyr-nVal-;
$R_2$ is cyclohexylmethyl;
$R_3$ is H;
$R_a$ is H; and
$R_b$ is H.

* * * * *

UNITED STATES PATENT AND TRADEMARK OFFICE
CERTIFICATE OF CORRECTION

PATENT NO. : 5,114,927
DATED : May 19, 1992
INVENTOR(S) : Daniel G. Schirlin

It is certified that error appears in the above-identified patent and that said Letters Patent is hereby corrected as shown below:

At Column 2 Line 38, the patent reads: "nitro:" and should read: -- nitro;--.

At Column 3 Line 14, the patent reads: "Gly NHCH$_3$" and should read: --Gly-NHCH$_3$--.

At Column 3 Line 50, the patent reads: "R$_1$ is Phd 2P$_3$" and should read: --R$_1$ is P$_2$P$_3$--.

At Column 4 Line 30, the patent reads: "Butoxyloxycarbonyl" and should read: -- Butyloxycarbonyl--.

At Column 6 Line 28, the patent reads: "L-(O-meth yl)" and should read: --L-(O-methyl)--.

At Column 6 Line 31, the patent reads: "L-n-Valyl]6 methyl" and should read: --L-n-Valyl]-6-methyl--.

At Column 6 Line 35, the patent reads: "alanine L-n-Valyl]3-oxo" and should read: --alanine L-n-Valyl]-3-oxo--.

At Column 6 Line 50, the patent reads: "methyl) Tyrosyl" and should read: --methyl)-Tyrosyl--.

At Column 11 Line 11, the patent reads: "ethylacetate" and should read: --ethyl acetate--.

At Column 11 Line 34, the patent reads: "3hydroxy" and should read: --3-hydroxy--.

At Column 12 Line 12, the patent reads: "difluoro-3 hydroxy" and should read: --difluoro-3-hydroxy--.

UNITED STATES PATENT AND TRADEMARK OFFICE
CERTIFICATE OF CORRECTION

PATENT NO. : 5,114,927
DATED : May 19, 1992
INVENTOR(S) : Daniel G. Schirlin

It is certified that error appears in the above-identified patent and that said Letters Patent is hereby corrected as shown below:

At Column 13 Line 12, the patent reads: " " and should read:
--4-Benzyloxycarbonylamino-2,2-difluoro-3-hydroxy butanamide --. , after "Example".

At Column 14 Line 27, the patent reads: "ethylacetate" and should read:
--ethyl acetate--.

At Column 15 Line 2, the patent reads: "N4" and should read: --$N^4$--.

At Column 16 Line 29, the patent reads: "N-lisoamyl" and should read: --$N^1$-isoamyl--.

At Column 16 Line 45, the patent reads: "$N^1$-isoamyl-$N^1$-[N" and should read:
--$N^1$-isoamyl-$N^4$-[N--.

At Column 17 Line 4, the patent reads: "hydroxy pentanoic" and should read:
--hydroxy-pentanoic--.

Signed and Sealed this

Seventh Day of December, 1993

Attest:

Attesting Officer

BRUCE LEHMAN

Commissioner of Patents and Trademarks